(12) United States Patent
Matthys-Mark et al.

(10) Patent No.: US 7,316,688 B2
(45) Date of Patent: Jan. 8, 2008

(54) CUTTING AND FORMING DEVICE

(75) Inventors: Romano Matthys-Mark, Fideris (CH); Hans Gelpke, Wiesendangen (CH)

(73) Assignee: Synthes (U.S.A.), West Chester, PA (US)

( * ) Notice: Subject to any disclaimer, the term of this patent is extended or adjusted under 35 U.S.C. 154(b) by 0 days.

(21) Appl. No.: 11/233,255

(22) Filed: Sep. 21, 2005

(65) Prior Publication Data
US 2006/0149290 A1 Jul. 6, 2006

Related U.S. Application Data

(63) Continuation of application No. PCT/CH03/00183, filed on Mar. 21, 2003.

(51) Int. Cl.
*A61B 17/58* (2006.01)
(52) U.S. Cl. .......................... 606/74; 606/103; 30/240
(58) Field of Classification Search ................ 606/101, 606/104, 74, 103, 180; 30/240, 278, 279.2, 30/90, 90.1
See application file for complete search history.

(56) References Cited

U.S. PATENT DOCUMENTS

| 2,428,650 | A | * | 10/1947 | Brunner ........................ 83/199 |
| 2,951,288 | A | * | 9/1960 | Holmes ........................ 30/240 |
| 2,963,785 | A | * | 12/1960 | Dilling .................... 73/864.44 |
| 3,315,669 | A | | 4/1967 | Rhodes |
| 3,370,353 | A | * | 2/1968 | Bernard et al. ............... 30/233 |
| 4,051,596 | A | | 10/1977 | Hoffmann |
| 5,445,641 | A | * | 8/1995 | Frigg et al. ................. 606/104 |
| 5,980,547 | A | | 11/1999 | Rinner |

FOREIGN PATENT DOCUMENTS

| DE | 1277515 | 9/1968 |
| DE | 8708571 | 8/1987 |
| EP | 0928602 | 7/1999 |

* cited by examiner

*Primary Examiner*—Stephen Choi
(74) *Attorney, Agent, or Firm*—Fay Kaplun & Marcin, LLP

(57) ABSTRACT

A cutting and forming device includes an outer sleeve, an inner sleeve, and a housing. The outer sleeve has a longitudinal axis, a front end, a rear end, and a borehole having an borehole axis. The inner sleeve, can be rotated in the outer sleeve's borehole and includes a front end, a rear end, and a borehole having a borehole axis. The housing with a central axis has a front end, a rear end, and a cavity which accommodates the outer sleeve and passes through the housing parallel to the central axis. The front end of the inner sleeve has a circular cutting edge which is concentric with the borehole axis of the inner sleeve, and the borehole at the front end of the outer sleeve has a constriction whose longitudinal axis is parallel to the borehole axis of the outer sleeve.

18 Claims, 3 Drawing Sheets

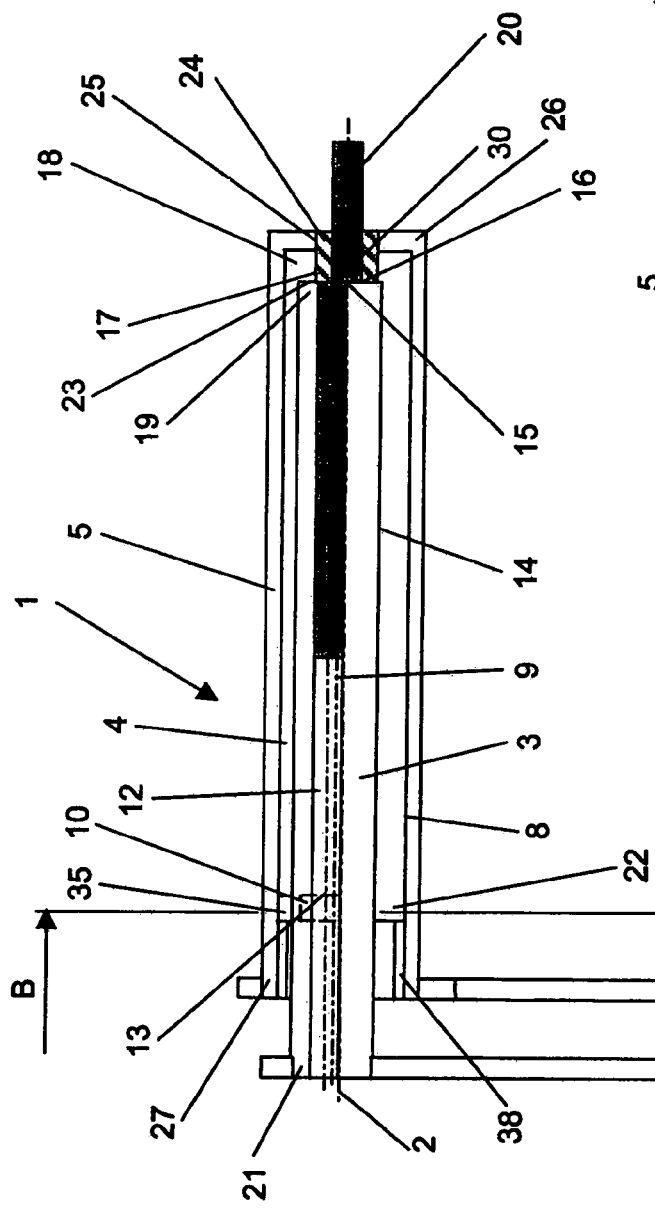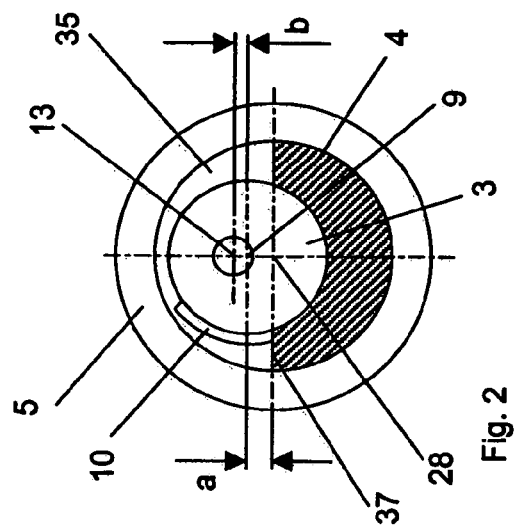
Fig. 1
Fig. 2

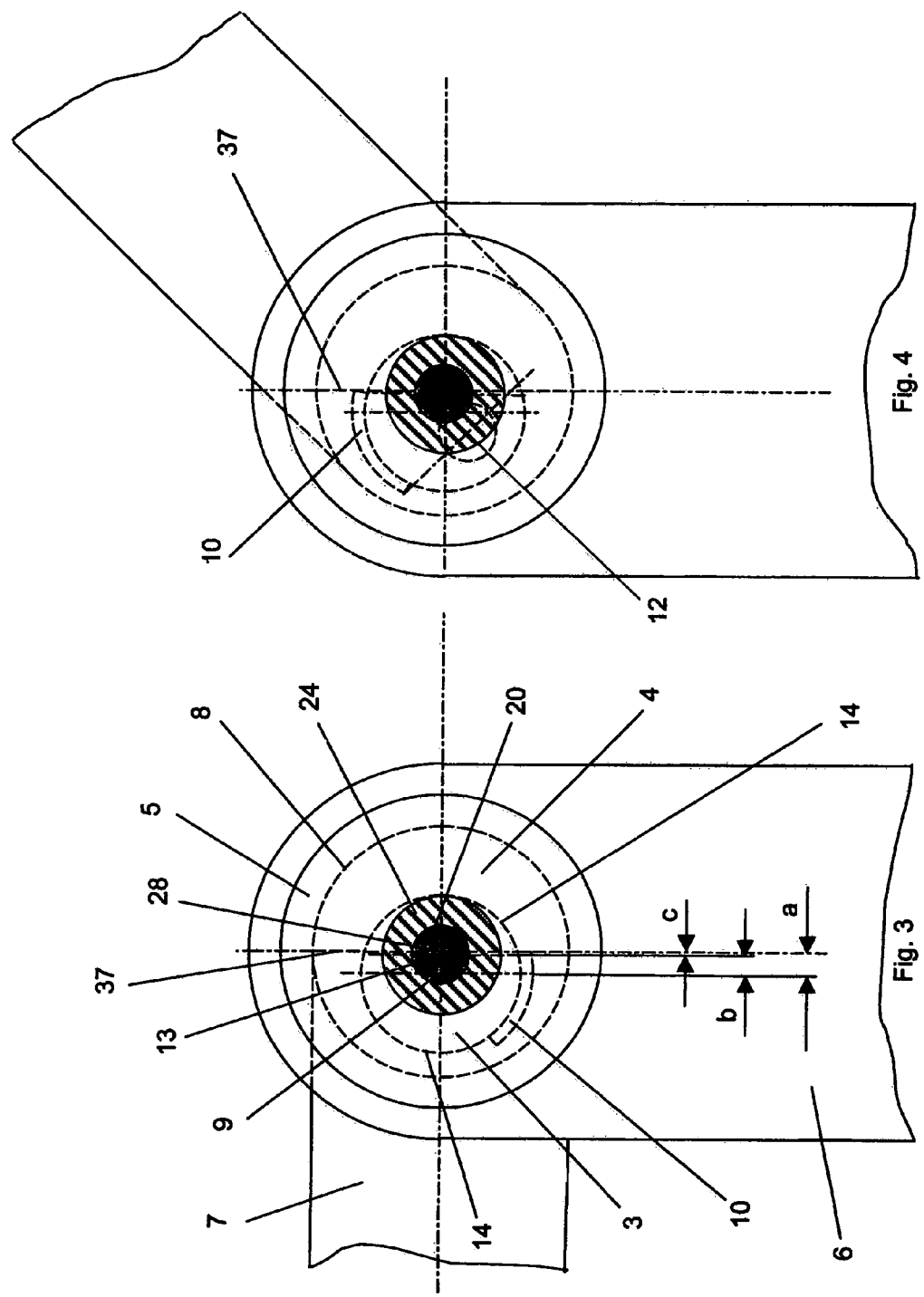

CUTTING AND FORMING DEVICE

CROSS-REFERENCE TO RELATED APPLICATION

This application is a continuation of International Patent Application No. PCT/CH2003/000183, filed Mar. 21, 2003, the entire contents of which is expressly incorporated herein by reference.

TECHNICAL FIELD

The present invention generally relates to a device for cutting a wire and, at the same time, forming a sleeve for protecting the end of the wire.

BACKGROUND OF THE INVENTION

Kirschner wires or similar fixation elements frequently are used, for example, when conducting a surgical intervention or for stabilizing bones or bone fragments by means of an external fixator. Depending on the application, these wires must be brought to a desired length after they are fixed at the bone or at the bone fragment. Kirschner wires or fixation elements may be severed with wire cutting tools in order to shorten them.

U.S. Pat. No. 4,051,596 (Hofmann) discusses a wire cutting tool with two concentric sleeves which can be rotated within one another. Hofmann wire cutting tool comprises cutting edges, which are concentric with the longitudinal axis of the sleeves. A disadvantage is that, when used during a surgical intervention, the portion of the Kirschner wire remaining at the bone or bone fragment having been squeezed as the wire is severed forms a bur, sharp edges, or pointed ends at the place of cutting. This can cause irritations at the adjoining soft parts.

SUMMARY OF THE INVENTION

The present invention provides a remedy for the above-discussed disadvantage. An object of the present invention to provide a device which is able to produce a bur-free cut through a Kirschner wire and to press onto the end of the severed Kirschner wire (or other fixation element) a protective sleeve.

The present invention accomplishes the objectives set out above with a cutting and forming device comprising an outer sleeve, an inner sleeve, and a housing. The outer sleeve includes a second longitudinal axis, a first front end, a first rear end, and a first borehole having an first borehole axis passing longitudinally through the outer sleeve. The inner sleeve, capable of being rotated in the first borehole coaxially to the first axis of the first borehole, includes a second front end, a second rear end, and a second borehole having a second borehole axis passing through the inner sleeve longitudinally. The housing with a central axis has a front end, a rear end, and a cavity which accommodates the outer sleeve and passes through the housing parallel to the central axis. The second front end of the inner sleeve has a circular cutting edge which is concentric with the second borehole axis, and the first borehole at the first front end of the outer sleeve has a constriction whose third longitudinal axis is parallel to the first borehole axis and is at a distance a>0 from the from the first borehole axis. The second borehole axis of the second borehole extends parallel to the first borehole axis of the first borehole at a distance b>0 therefrom.

Advantages achieved by the present invention are that a bur-free severing of a Kirschner wire or of a different fixation element is possible, no sharp edges or pointed ends are formed during the severing process, and because the Kirschner wire is guided in a borehole, a severed surface, perpendicular to the longitudinal axis, can be produced and the rear end of the Kirschner wire may be provided with a protective sleeve without requiring any refinishing, such as the removal of sharp edges or pointed ends.

Other objectives and advantages, in addition to those discussed above, will become apparent to those skilled in the art during the course of the description of the embodiments of the invention which follows. In the description, reference is made to accompanying drawings, which form a part thereof, and which illustrate examples of the invention. Such examples, however, are not exhaustive of the various embodiments of the invention, and therefore, reference is made to the claims that follow the description for determining the scope of the invention.

BRIEF DESCRIPTION OF THE DRAWINGS

The cutting and forming device and the method of use are explained in even greater detail in the following exemplary drawings. The cutting and forming device and its method of operation may be better understood by reference to the following drawings, wherein like references numerals represent like elements. The drawings are merely exemplary to illustrate the structure, operation and method of use of the cutting and forming device and certain features that may be used singularly or in combination with other features and the invention should not be limited to the embodiments shown.

FIG. 1 shows a longitudinal view of an embodiment of the inventive device,

FIG. 2 shows a section B-B view the embodiment of the inventive device shown in FIG. 1, FIG. 3 shows a view from A of the embodiment of the inventive device shown in FIG. 1, with sleeves and housing positioned for introducing the sleeve, protecting the end of the wire, and the Kirschner wire, FIG. 4 shows a view from A of the embodiment of the inventive device shown in FIG. 1, with the sleeves rotated relative to one another.

DESCRIPTION OF THE PREFERRED EMBODIMENTS

Figure 5:
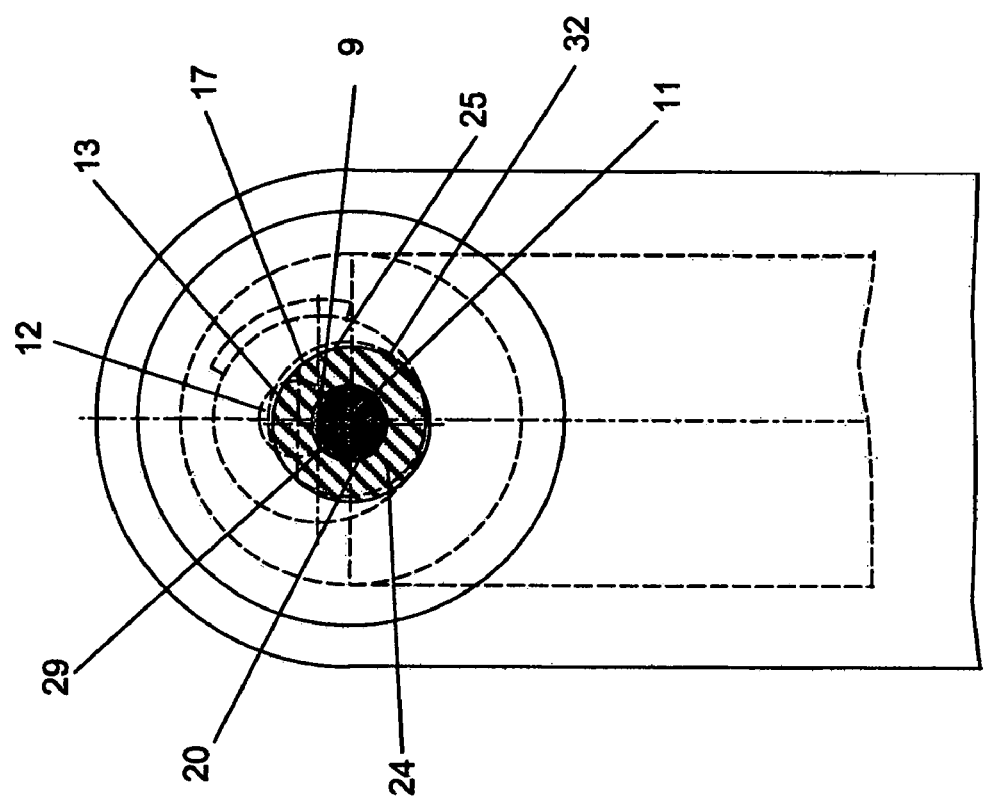
FIG. 5 shows a view from A of the embodiment of the inventive device shown in FIG. 1, after the sleeves are twisted relative to one another and with respect to the housing.

An embodiment of the present invention, a cutting and forming device 1, is shown in FIG. 1. The cutting and forming device 1 includes a hollow cylindrical housing 5 with a cavity 8, and having a longitudinal axis 2. The cavity 8 at the front end 25 of the housing 5 has a borehole 25 with a longitudinal axis 29, which is parallel to the central axis of the housing 5, from which it is removed by a distance "c". The diameter of borehole 25, corresponds to the external diameter "D" of a sleeve 24 protecting the end of a Kirschner wire 20. A handrail 6 is disposed perpendicularly to the longitudinal axis 9 of the cavity 8 at the rear end 27 of the housing 5. The handrail 6 is used in conjunction with an actuating lever 7 attached to at least one of two sleeves 3 and 4. The actuating lever 7 allows for a greater shear force to be applied to the Kirschner wire 20.

The cutting and forming device 1 also includes two sleeves 3 and 4 which are disposed in the cavity 8 of the housing 5 in such a manner, that they can be rotated about the longitudinal axis 2. The two sleeves 3 and 4 may be configured in such a way that a borehole 12 in the inner sleeve 3 serves to accommodate a fixation element or a Kirschner wire 20 and has a diameter "d". A constriction 17 of a borehole 14 in the outer sleeve 4 serves to accommodate a sleeve 24 to protect the end of the wire. The diameter of the sleeve "D", being equal to the diameter of the borehole 25, is greater than the diameter of the Kirschner wire, "d".

Specifically, the outer sleeve 4 may have a longitudinal axis 28, and may include an eccentric borehole 14 which has a borehole axis 9 that passes longitudinally through the outer sleeve 4. The outside of the outer sleeve 4 is configured circularly, cylindrically and concentrically with the longitudinal axis 28. The constriction 17 at the front end 18 of the outer sleeve 4 results in a supporting surface 23 being formed perpendicular to the borehole axis 9. When the inner sleeve 3 is disposed in the borehole 14 of the outer sleeve 4, the front end 19 of the inner sleeve 3 may abut against the supporting surface. By means of this configuration, it can be achieved that a first circular cutting surface 15 can be produced at the outlet of a borehole in the inner sleeve and a second, circular cutting edge 16, concentric with the longitudinal axis 11 of the constriction 17, can be produced at the transition of the supporting surface 23 to the constriction 17 in the outer sleeve 4. Because of the eccentricity of the axis of the borehole in the interior of the sleeve 24 and the longitudinal axis of the constriction 17, the Kirschner wire 20 can be sheared off by rotating the two sleeves 3 and 4 relative to one another.

The inner sleeve 3 is mounted in borehole 14 such that it can be rotated coaxially about the borehole axis 9 and has a borehole 12 with a borehole axis 13 which is eccentric with respect to the borehole axis 9. On the outside, the inner sleeve 3 is configured circularly, cylindrically and coaxially with the borehole axis 9. Borehole 12 accommodates a Kirschner wire 20 or a different fixation element. In one embodiment, the actuating lever 7 is attached perpendicularly to the longitudinal axis 9 of the cavity 8 at the rear end 21 of the inner sleeve 3.

Furthermore, the outer sleeve 4, at its rear end 22, may be constructed as a half shell, such that a recess 35 with two stop surfaces 37, parallel to the longitudinal axis 2, is formed. A catch 10, protruding radially at the rear end 21 of the inner sleeve 3, comes to rest at an angle of rotation, between the inner and outer sleeves 3 and 4, of 135° at one of the stop surfaces 37. The catch 10 is freely movable about an angle of rotation □ within the recess 35 when the sleeves are rotated relative to one another. The angle of rotation □ preferably ranges from 90° to 180°. At the end of a cutting process, the catch 10 and the stop surface 37 lie against one another in the recess 35, so that the two sleeves 3 and 4 cannot be rotated further relative to one another but can be rotated together relative to the housing 5. Further rotation of the two sleeves 3 and 4 relative to the housing 5 causes a pressing process between the sleeve 24, protecting the end of the wire, and the Kirschner wire 20, to be carried.

A Kirschner wire 20 or a different fixation element and a sleeve 24 may be introduced into the cutting and forming device 1. The sleeve 24 has a rear end, a front end and a central borehole 30. Due to the eccentricity "a" of the borehole axis 9 of the borehole 14 of the outer sleeve, which accommodates the inner sleeve 3, with respect to the longitudinal axis 2, and the eccentricity "b" of the borehole axis 13 of the borehole 12 of the inner sleeve 3, which accommodates the Kirschner wire 20, and of the borehole axis 9, the inner sleeve 3 can be brought into a rotative position relative to the outer sleeve 4 in which the borehole 12 is aligned with the central borehole 30 in the sleeve 24. The sleeve 24 which may be used to protect the end of the wire can be pushed parallel to the longitudinal axis 11 into the constriction 17, where the rear end of the sleeve 24 may axially contact the front end 19 of the inner sleeve 3. Further, the central borehole 30 of the sleeve 24 is provided at the rear end with a cutting edge, which is concentric with the central borehole 30. Furthermore, in this position of the inner sleeve 3 (FIG. 3), the Kirschner wire 20 can be introduced through the borehole 25 at the front end 26 of the housing 5, through the central borehole 30 in the sleeve 24, which protects the end of the wire, and into the borehole 12 in the inner sleeve 3. Specifically, because of the configuration of the eccentricities "a", "b", and "c" with the condition that a−b=c (FIG. 3), in the relative position of the inner sleeve 3, the outer sleeve 4 and the housing 5 shown in FIG. 3, a sleeve 24 can be introduced into the borehole 25 at the front end 26 of the housing 5 and into the constriction 17 at the front end 18 of the outer sleeve 4 coaxially with the borehole axis 13 of the borehole 12. A Kirschner wire 20 can then be introduced through the central borehole 30 of the sleeve 24, protecting the end of the wire, coaxially with the borehole axis 13 into the borehole 12. The position, shown in FIG. 3, is distinguished owing to the fact that the inner sleeve 3 and the outer sleeve 4 are positioned so that the three eccentricities "a", "b" and "c" lie on a straight-line and fulfill the condition a=b+c (FIG. 3).

The eccentricities "a", "b", and "c" preferably fall within the following ranges:
 eccentricity a between 0.2 mm and 0.8 mm,
 eccentricity b between 0.2 mm and 0.8 mm, and
 eccentricity c between 0.05 mm and 0.4 mm.

In one embodiment, the distances "a" and "b" are such, that "a" is greater than "b". As discussed later, because of the different eccentricities of the boreholes in the inner sleeve 3 and the constriction 17, a Kirschner wire 20 or different fixation element can be severed by rotating the inner sleeve 3 relative to the outer sleeve 4 and, at the same time, the sleeve 24, protecting the end of the wire, can be squeezed onto the end of the wire.

Because of the configuration of the borehole 12 in the inner sleeve 3 a first circular cutting edge 15 surrounding the Kirschner wire 20 may be achieved at the front end of the inner sleeve 3. The sleeve 24 is held fast radially in the outer sleeve 4 by the configuration of the constriction 17, such that a second circular cutting edge 16, surrounding the Kirschner wire 20, is formed at the inner (rear) end of the sleeve 24 by the wall of the central borehole 30 of the sleeve 24.

More specifically, the first cutting edge 15 is formed by the circular line-shaped, sharp edged border at the outlet of the borehole 12 at the front end 19 of the inner sleeve 3. The sleeve 24, introduced into the constriction 17 of the outer sleeve 4, is configured with a central borehole 30 for accommodating the Kirschner wire 20. The ends of the central borehole 30 have a sharp edge. By these means, the second cutting edge 16, which is directed against the first cutting edge 15, is formed at the end of the sleeve 24. By twisting the two sleeves 3 and 4 relative to one another (FIGS. 4 and 5), the Kirschner wire 20 is severed by means of a shearing motion between the cutting edges 15 and 16, caused by the rotation of the latter eccentrically to one another. That is, because the longitudinal axis of the constriction 17 and the borehole axis 13 of the borehole 12 in the interior sleeve 3 are disposed eccentrically to the axis of rotation of the inner sleeve 3, which is formed by the longitudinal axis of the circularly cylindrical inner sleeve 3 coinciding with the borehole axis 9 in the outer sleeve 4, the Kirschner wire 20 is sheared off between the first and second cutting edges 15 and 16 when the inner sleeve 3 is rotated relative to the outer sleeve 4.

As is evident from the above discussion, if a sleeve 24 is not used, the Kirschner wire 20 cannot be severed, because there is no second cutting edge. Accordingly, additional security can be attained such that the Kirschner wire 20 or different fixation element can be shortened only when the sleeve 24, protecting the end of the wire, is inserted in the cutting and forming device 1.

Aside from cutting the Kirschner wire 20, the sleeve 24, protecting the end of the wire, can be fastened to the rear end of the Kirschner wire 20 in the same cutting step. The fasting is accomplished by pressing the side wall 32 of the sleeve 24 against the Kirschner wire 20 by means of the eccentric arrangement of the constriction 17 at the outer sleeve 4 and the borehole 25 at the front end 26 of the housing 5. The compressed fit connection can be established between the sleeve 24, protecting the end of the wire, and the Kirschner wire 20 by rotating the outer sleeve 4 in the cavity 8 of the housing 5. When the catch 10 abuts one of the stop surfaces 37 of the outer sleeve, further rotation of the actuating lever 7, relative to the handrail 6, causes the two sleeves 3 and 4 to be rotated relative to the housing 5 (FIG. 5). As a result, the constriction 17 together with the sleeve 24 introduced into the constriction 17, are rotated in the housing 5 with respect to the borehole 25. Due to the eccentric arrangement of the borehole axis 29 of the borehole 25 relative to the longitudinal axis 11 of the constriction 17, the sleeve 24 is squeezed by the walls of the borehole 25 and of the constriction 17 and fixed onto the Kirschner wire 20 which was introduced into the central borehole 30 of the sleeve 24.

The invention claimed is:

1. A device for cutting a guide wire and a Kirschner wire and, at the same time, attaching a protective sleeve for protecting the end of the wire, said device comprising:
    an outer sleeve having a second longitudinal axis, a first front end, a first rear end, and a first borehole having an first borehole axis passing longitudinally through the outer sleeve, the first borehole at the first front end of the outer sleeve has a constriction whose third longitudinal axis is parallel to the first borehole axis and is at a distance a>0 from the first borehole axis;
    an inner sleeve capable of being rotated in the first borehole coaxially to the first axis of the first borehole having a second front end, a second rear end, and a second borehole having a second borehole axis passing through the inner sleeve longitudinally, the second borehole axis extends parallel to the first borehole axis of the first borehole at a distance b>0 therefrom; and
    a housing with a central axis, a front end, a rear end, and a cavity which accommodates the outer sleeve and passes through the housing parallel to the central axis, wherein the second front end of the inner sleeve has a circular cutting edge which is concentric with the second borehole axis,
    wherein the constriction accommodates the protective sleeve and compress fits the protective sleeve onto the wire when the outer sleeve and inner sleeve are rotated with respect to each other.

2. A device according to claim 1, wherein:
    the second borehole of the inner sleeve accommodates the guide wire or the Kirschner wire and has a diameter d;
    the constriction has a diameter D; and
    D being greater than d.

3. A device according to claim 2, wherein the protective sleeve for protecting the end of the wire includes a third rear end, a third front end, and a central borehole.

4. A device according to claim 3, wherein the protective sleeve which protects the end of the wire is pushed parallel to the third longitudinal axis into the constriction and the third rear end of the sleeve is brought axially into contact with the second front end of the inner sleeve.

5. A device according to claim 3, wherein walls of the central borehole of the sleeve has at the third rear end encompass a second concentrically cutting edge.

6. A device according to claim 1, wherein a>b.

7. A device according to claim 1 wherein at least one of the outer sleeve and inner sleeve is equipped at its rear end with an actuating lever which is disposed transversely to the borehole axes.

8. A device according to claim 7, wherein the actuating lever is fastened at the second rear end of the inner sleeve.

9. A device according to claim 1, wherein a flat supporting surface, perpendicular to the first borehole axis, is formed by the constriction, and the second front end of the inner sleeve abuts the flat supporting surface.

10. A device according to claim 1, wherein the cavity at the front end of the housing includes a borehole with a longitudinal axis which is parallel to the central axis at a distance c>0 from the central axis.

11. A device according to claim 10, wherein the diameter of the borehole corresponds to the external diameter of the protective sleeve.

12. A device according to claim 10, wherein the inner sleeve includes a catch and the outer sleeve a recess, wherein the catch being freely movable about an angle of rotation $\alpha$ within the recess when the inner sleeve and outer sleeve are rotated relative to one another.

13. A device according to claim 12, wherein the angle of rotation ranges from about 90° to about 180°.

14. A device according to claim 10, wherein the distance "c" is between about 0.05 mm and about 0.4 mm.

15. A device according to claim 14, wherein the distance "c" is between about 0.1 mm and about 0.3 mm.

16. A device according to claim 1, wherein the distance "a" is between about 0.2 mm and about 0.8 mm.

17. A device according to claim 16, wherein the distance "a" is between about 0.4 mm and about 0.6 mm.

18. A device according to claim 1, wherein the distance "b" is between about 0.2 mm and about 0.8 mm.

* * * * *